United States Patent [19]

Zamba et al.

[11] 4,443,935

[45] Apr. 24, 1984

[54] PROCESS FOR MAKING ELECTROSURGICAL SCALPEL PENCIL

[75] Inventors: Gene Zamba, Oldsmar; Carl Foltz, North Largo, both of Fla.

[73] Assignee: Trident Surgical Corporation, Clearwater, Fla.

[21] Appl. No.: 353,479

[22] Filed: Mar. 1, 1982

[51] Int. Cl.³ .................. H01H 11/06; A61B 17/36
[52] U.S. Cl. ...................................... 29/622; 29/825; 128/303.14; 128/303.17
[58] Field of Search .............. 29/622, 825, 592 R; 128/303.14, 303.17; 200/6 C, 153 K

[56] References Cited

U.S. PATENT DOCUMENTS

| | | | |
|---|---|---|---|
| 3,801,766 | 4/1974 | Morrison, Jr. | 128/303.14 X |
| 4,034,761 | 7/1977 | Prater et al. | 128/303.17 X |
| 4,112,950 | 9/1978 | Pike | 128/303.17 X |
| 4,170,234 | 10/1979 | Graham | 128/303.17 X |

*Primary Examiner*—Carl E. Hall
*Attorney, Agent, or Firm*—Gipple & Hale

[57] ABSTRACT

A process for making an electrosurgical pencil with rocker switch for holding and controlling a monopolar electrosurgical scalpel blade, wherein the rocker switch pivots on the exterior of the pencil body and is isolated from the interior of the body by a flexible waterproof seal. In the process for manufacturing the electrosurgical pencil, a cable portion having at least a common conductor, first signal conductor, and second signal conductor is selected, clips are attached to each end of the three conductors of the cable portion, and a spring contact and a clip attached to one end of the common conductor are installed in a pencil body portion so that a central portion of the spring contact is held adjacent a switch seat. Clips attached to the first and second signal conductors are then mounted within the body portion beneath opposite ends of the switch seal and spaced apart from the spring contact, and a second body portion is sealed to the first body portion to create a unitary electrosurgical pencil body. The three clips at the opposite end of the cable from the body are installed in an asymmetrical polarized generator connector for electrical connection to an electrosurgical generator, and a seal and rocker switch are attached to the switch seat above the spring contact, so that finger pressure on the rocker switch will deflect the seal and place the spring contact in electrical connection with either of the wire clips within the body attached to the first or second signal conductors.

11 Claims, 9 Drawing Figures

PROCESS FOR MAKING ELECTROSURGICAL SCALPEL PENCIL

BACKGROUND OF THE INVENTION

The present invention relates to surgical instruments and, more specifically, to a disposable electrosurgical pencil capable of selectively providing cut or coagulate waveforms to a scalpel electrode mounted on the pencil.

Various devices have been developed and disclosed to exploit the reaction of living tissue to an applied electrical current. High current applied over a relatively small area of tissue can provide rapid and localized transformations. For instance, many systems have been developed to apply radio frequency current through a thin scalpel electrode, which is collected and returned via a second electrode applied over a wide area of tissue remote from the surgical site. These systems generally provide two modes of operation: cut, which is analogous to the function of the traditional knife scalpel, and coagulate, which produces hemostasis.

In a typical surgical procedure utilizing electrosurgical techniques, a physician may desire to alternate the mode of operation of the electrosurgical apparatus. In order to minimize the severity of surgical trauma and the risk of infection and other complications, it is always important to minimize the time and attention taken away from the patient to control surgical instruments of any complexity, including electrosurgical systems. To this end, a variety of electrosurgical scalpel electrode handles, known as electrosurgical pencils, have been developed utilizing control switches so that the surgeon may alternate modes without removing his or her eyes, hands, or attention from the patient.

U.S. Pat. No. 4,170,234 discloses an electrosurgical pencil with a rocker switch for selection of mode of operation. As is typical among such devices, the pencil is connected to an electrosurgical generating apparatus by a cable comprising three conductors: a first signal line, a second signal line, and a common line which serves not only to return the selected control signal to the generator, but also to deliver current to the scalpel electrode. Thus, all three conductors are maintained at high voltage, with the control signal conductors differing in voltage slightly from the common conductor so that a relatively small current will serve to select the mode of operation desired. The rocker switch maintains constant contact through spring contacts with the common conductor. The spring contacts also serve to support the fulcrum of the rocker switch within the housing of the pencil. The two control signal conductors and the common conductor lie in a plane below the rocker switch, and the metallic bottom surface of the rocker switch is shaped so as to contact with one or the other of the signal conductors on either side of the common conductor when the appropriate end of the rocker switch is depressed. Among the disadvantages inherent in the disclosed pencil is the lack of a moisture-proof seal around the rocker switch, and the lack of a fixed fulcrum for the rocker switch. The floating fulcrum allows either end of the switch to be jammed beneath the surface of the pencil casing, thereby delivering current to the scalpel electrode when the surgeon may believe it to be inoperative.

U.S. Pat. No. 4,112,950 discloses another electrosurgical pencil utilizing a three-conductor current control and delivery circuit. Two push-button switches rest atop a conductor and pivot around an internal fulcrum defined by posts and a casing extension. The common conductor and the control signal conductors are connected to posts beneath the conductor. When a button is depressed, it contacts and connects a common conductor post to a signal conductor post. It is evident that both buttons could be depressed simultaneously, because they share no rigid common body to prevent such an occurrence. Moreover, this system like the previous system lacks a moisture-proof seal around the switch contacts as well as a jam-proof switch due, again, to the use of an internal fulcrum.

Another electrosurgical pencil is disclosed in U.S. Pat. No. 4,034,761. This device is also devoid of a moisture-proof seal around its rocker switch, and is provided with an internal fulcrum for the switch which may allow jamming within the casing of the pencil. Moreover, this device also permits pressure to be exerted on both ends of the rocker switch simultaneously to make contact between all three conductors, thereby creating a potentially dangerous electrical circuit.

The safe operation of an electrosurgical pencil is vital not only to the patient, but also to the surgeon responsible for the patient's wellbeing and survival. Unexpected injury by a high current to either the patient or the surgeon can pose grave consequences. Dangerous electrical circuits can be completed if moisture, such as the typical body fluids which abound during surgery, accidentally reach the interior of the electrosurgical pencil. Since the surgeon's fingers frequently come in contact with the patient as well as the switch of the electrosurgical pencil, it is especially important to prevent the entrance of moisture from fingers around the switch. Because the surgeon may wish to set aside the electrosurgical pencil from time to time during surgery, it is important that the switch be arranged to prevent accidental jamming of the switch in an "on" position when finger pressure is removed. It is also especially important to provide a switch structure which eliminates the possibility of connection of all three conductors at one time.

Thus, it is clear that there exists a need in the art for an electrosurgical pencil with a control switch structure which prevents the entrance of moisture into the pencil, avoids the possibility of jamming the switch to energize the scalpel electrode when finger pressure is removed from the switch, prevents stripping of the electrical contacts when the cable or cord is pulled, and eliminates the possibility of simultaneously connecting all three conductors by inadvertent finger pressure. Additionally, there exists the need for a low cost disposable electrosurgical pencil of greatly simplified internal construction, and an economical process for manufacturing same, which allows fast assembly with reliable, easily insertable operating components, labor cost reduction, and a sturdy construction suitable for use in a medical environment.

SUMMARY OF THE INVENTION

The present invention provides an electrosurgical switch pencil comprising a scalpel electrode mounted in a two piece injection molded casing, a three-conductor current control and delivery circuit positioned within the casing, a switch on the casing for selection of either of two modes of current delivery, and an insulated conductor cable terminating in an asymmetrical polarized connector for electrical attachment to an electrosurgical generator system. The switch of the electrosurgical pencil comprises a rocker switch rotating about a fulcrum on the exterior of the casing, thus eliminating the possibility of jamming either end of the rocker switch within the casing to inadvertently maintain current. The fulcrum is fixed rather than floating, so that simultaneous pressure to contact all three conductors within the casing is prevented. A flexible moisture-proof seal is positively locked between the rocker switch and the conductors, to prevent entrance of moisture into the casing. Placed against the inside of the seal opposite the rocker switch is a flexible spring contact which extends from the mounting bore of the scalpel electrode past the switch to the terminus of the conductor cable. The spring contact maintains the rocker switch in a neutral position when no finger pressure is applied, and deflects with the flexible seal when finger pressure is applied to contact either of two fixed contact posts beneath the ends of the rocker switch within the casing. The two posts are electrically connected, respectively, to the two control signal conductors of the cable, and the spring contact is connected to the common conductor of the cable. A novel manufacturing process for the inventive apparatus is also disclosed.

In the process, an electrical cable is stripped and the ends of the conductor wires are provided with contact clips. One half of the pencil housing is handled and a conductor member is mounted into the housing half. The clips of the proximal end of the wires are loaded into the half of the housing of the switch pencil and the other half of the housing is placed on the loaded half and sonically welded together. The distal ends of the wires are placed into a plug adapted to connect to an electrosurgical generator. The seal, switch, and cap are placed on the housing and the cap is sonically welded to the housing.

These and other objects and advantages of the present invention will be more fully appreciated by reference to the following detailed description of the preferred embodiment, when read in conjunction with the accompanying drawings.

DETAILED DESCRIPTION OF THE DRAWINGS

Figure 1:
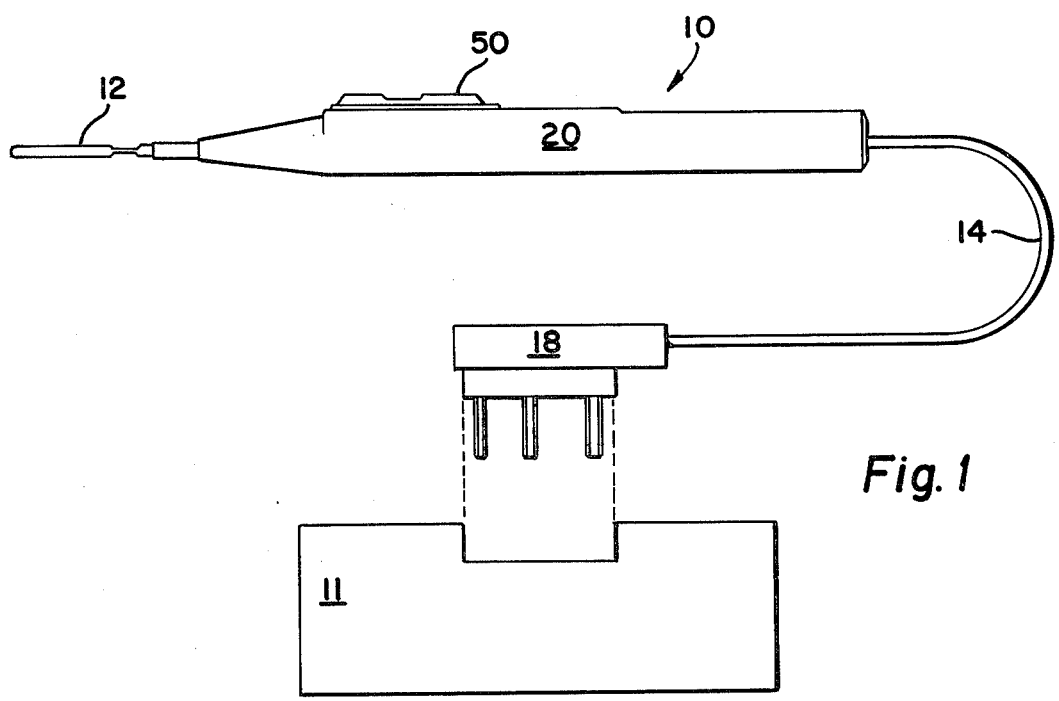
FIG. 1 is a side elevational view of the present inventive apparatus.

The best mode and preferred embodiment of the present inventive apparatus is disclosed in FIGS. 1-5. Turning to FIG. 1, the inventive apparatus is generally indicated at 10 and comprises a housing 20, an electrosurgical blade 12 extending from the proximal end of housing 20, a control switch 50 on the surface of housing 20, a cable 14 extending from the distal end of housing 20, and a connector plug 18 attached to an end of cable 14 remote from housing 20. The connector plug 18 is advantageously a three-contact asymmetric connector, so as to prevent inadvertent reversed installation of connector 18 to a current supply electrosurgical generator for the apparatus 10.

Any conventional dual-mode current supply or electrosurgical generator 11, which is shown as a block diagram as it is well known in the art and purchasable from several manufacturers, may be utilized in conjunction with the present inventive apparatus 10. As is also well-known in the art, the control circuit is established through the switch 50, cable 14 and connector 18 utilizes two control signal conductors and a common conductor which may be connected alternatively to either of the two control signal conductors by manipulation of switch 50. Simultaneously, the common conductor is also utilized to deliver current to a standard electrosurgical blade 12 which completes a current circuit through the body of the patient and a return electrode of substantial area attached to the patient.

Figure 2:
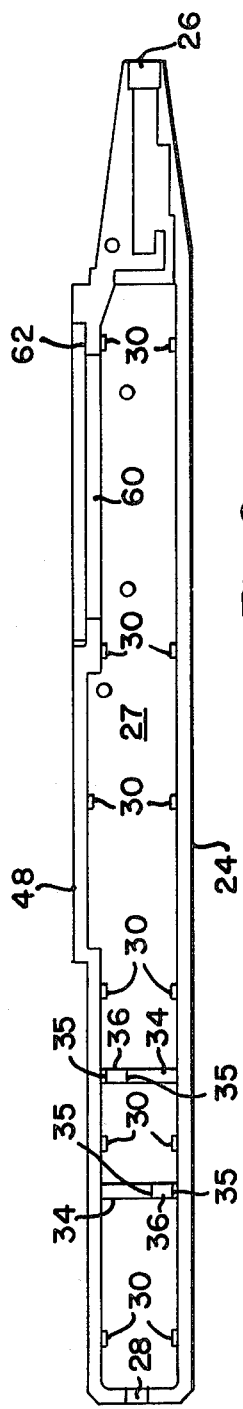
FIG. 2 is a side elevational view of the left half of the casing of the apparatus of FIG. 1.
Figure 3:
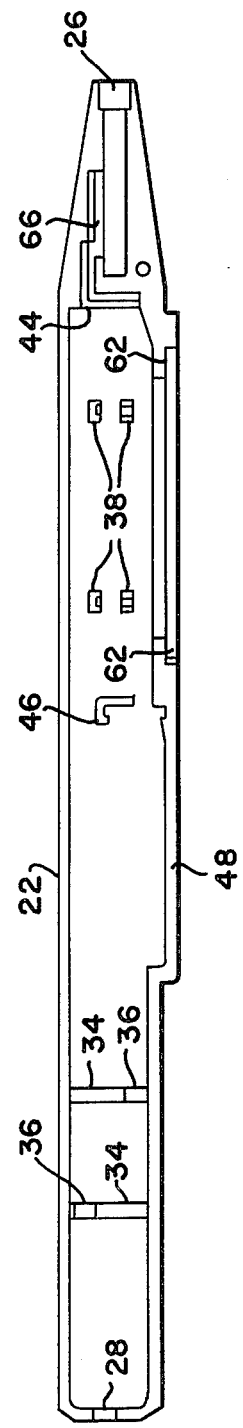
FIG. 3 is a side elevational view of the right half of the casing of the apparatus of FIG. 1.

The internal structure of housing 20 is illustrated in FIGS. 2 and 3. Housing 20 comprises an injection molded right half 22 and left half 24 which are sonically welded as described below to form a unitary housing 20. The housing halves are preferably constructed of a high impact styrene which can be gamma sterilized. A suitable styrene which can be used is COSDEN 825. Both halves 22 and 24 define a proximal socket bore 26 for removable installation of blade 12, an interior chamber 27 adapted to hold a conductor member and electrical contacts and wires, as well as distal aperture 28 for cable 14. A portion of the exterior of housing 20 forms a planar surface 48. This planar surface 48 in turn defines a rectangularly shaped switch seat 60 which communicates with the interior of the housing 20. Surrounding switch seat 60 is a recessed shoulder portion 62.

Adjacent distal aperture 28 in the rear of the housing, a plurality of support walls 34 are formed, which when both halves are welded together, extend across the chamber 27 of halves 22 and 24. Each support wall 34 defines a cable bore 36 for location of cable 14. Thus, strain relief is provided for cable 14 within housing 20 by installation of the cable through the bores 36 on a substantially non-linear or "S" shaped path. Pulling of the cable 14 or the housing 20 with respect to the pull provides force on shoulders 35 preventing stripping of the cable. A plurality of placement pins or bosses 30 extend outward from the edge of the interior wall of left half 24 in order to meet the interior wall of right half 22 and maintain alignment thereof during sealing of the halves to create the unitary housing 20.

Figure 4:
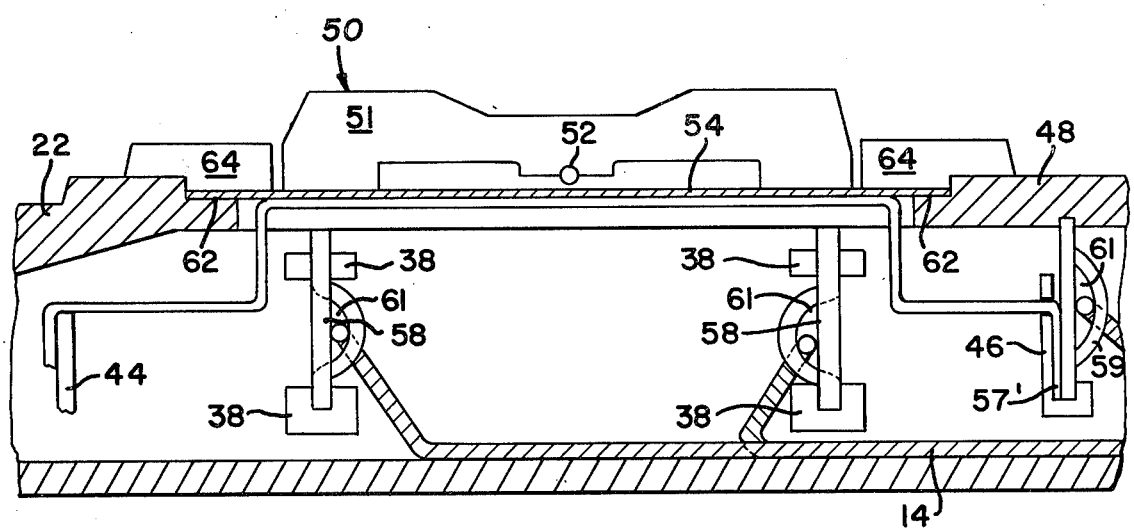
FIG. 4 is an enlarged isolated side view of the switch structure of the apparatus of FIG. 1.

FIG. 4 illustrates in detail the construction of switch 50 within switch seat 60. A flexible insulation seal or gasket 54 of rubber or other non-conductive material is extended across the entire switch seat 60 and rests on a rectangularly shaped shoulder 62 which surrounds seat 60. A switch body 51, preferably of the type commonly known as a rocker switch, is placed atop seal 54. Switch body 51 rotates on fulcrum or rocker pin 52 which is preferably integrally molded with the switch body. The fulcrum pin 52 extends across seal 54 and rests on opposite sides of seal seat 60 in fulcrum seats cut into the side wall of the seat or alternatively the switch cap frame 64.

The switch body 51 is surrounded by a switch cap 64 which extends from the planar surface 48 inward across shoulder 62 and seal 54, engaging shoulder 62 and retaining fulcrum pin 52 and seal 54. The cap squeezes the rubber gasket to render the switch area water-proof and shock-proof.

Figure 5:
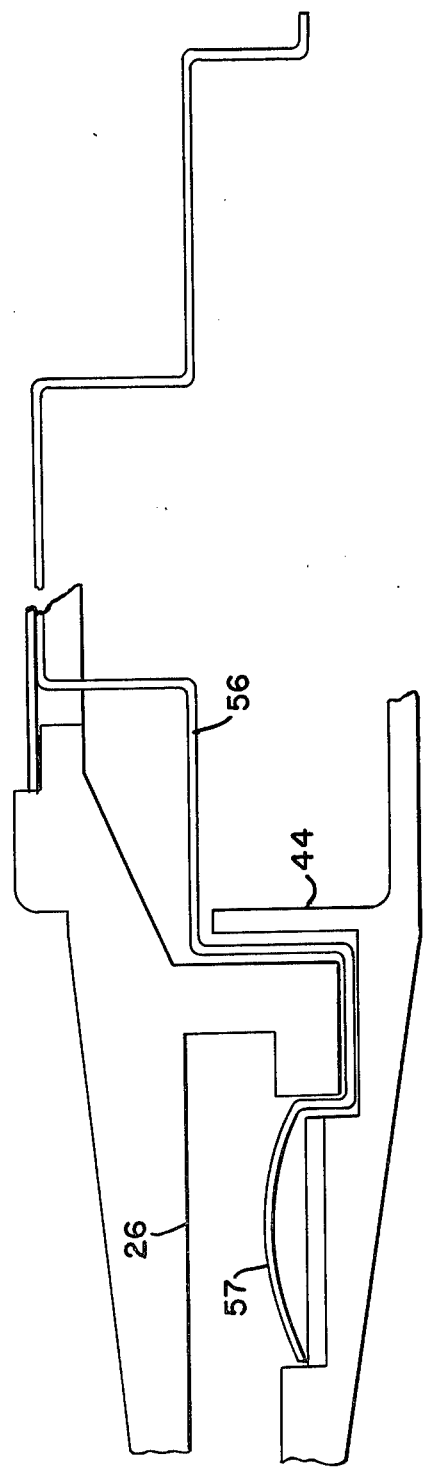
FIG. 5 is a side elevational view of the spring contact portion of the switch structure of FIG. 4.

A spring contact 56 as shown in FIG. 5 extends lengthwise adjacent seal 54 on the opposite side from switch body 51. Spring contact 56 may be made from any suitable metallic material which can carry current to blade 12 and maintain a springiness to force rocker switch 51 to the illustrated neutral position when not in use. This spring contact 56 is preferably a phosphor bronze spring temper with 0.2 mm nickel plate. However, a variety of other metallic materials are equally suitable.

Signal clips 58 and spring contact 56 are fixedly held to the right half 22 of body 20 as will be later explained. As is shown in FIG. 5, the proximal end 57 of spring contact 56 passes around retaining wall 44 and rests in contact seat 66 which is a part of proximal socket bore 26. The proximal end 57 forms an arc extending upward into the bore 26 and forms a flexible contact providing both secure electrical connection to, and physical restraint for blade 12. Returning to FIG. 4, spring contact 56 is restrained at its distal end 57' by support 46 integrally formed on half 22. A fixed clip 59 is secured between support 46 and an opposing interior surface of half 22, thus sandwiching the end 57' of spring contact 56 against support 46. Fixed clip 59 and signal clips 58 are preferably formed as a planar conductive clip with a central elbow aperture 61 formed by any well-known conventional method such as pressing, stamping or punching. The aperture 61 of the clips is sized to permit insertion and crimping of electrical wire to form a reliable electrical and mechanical joint. The common conductor wire of cable 14 is thus attached to fixed clip 59 and thereby to the sandwiched end of spring contact 56. Each of the two control signal conductor wires in cable 14 may likewise be attached to respective signal clips 58, which are mounted in contact mounts 38 integrally formed and exposed for contact with spring contact 56 beneath opposite ends of switch body 51.

The other end of cable 14 is mounted in a conductor plug 18 comprising a connector body 62 with distal end contacts 63. The contacts 63 are engaged by signal clips 58' and clip 59'. A plurality of posts 64 and 66 are formed in the connector body to provide strain relief if the cable 14 is pulled. The plug 18 is adapted to be connected in a standard manner to an electrosurgical generator 11.

Thus, when a surgeon depresses one end of switch body 51, seal 54 and spring contact 56 deflect towards and make contact with a signal clip 58 to complete an appropriate circuit. When pressure on switch body 51 is released, the springiness of contact 56 breaks contact with signal clip 58 and returns switch body 51 to the neutral position illustrated in FIG. 4.

Figure 6:
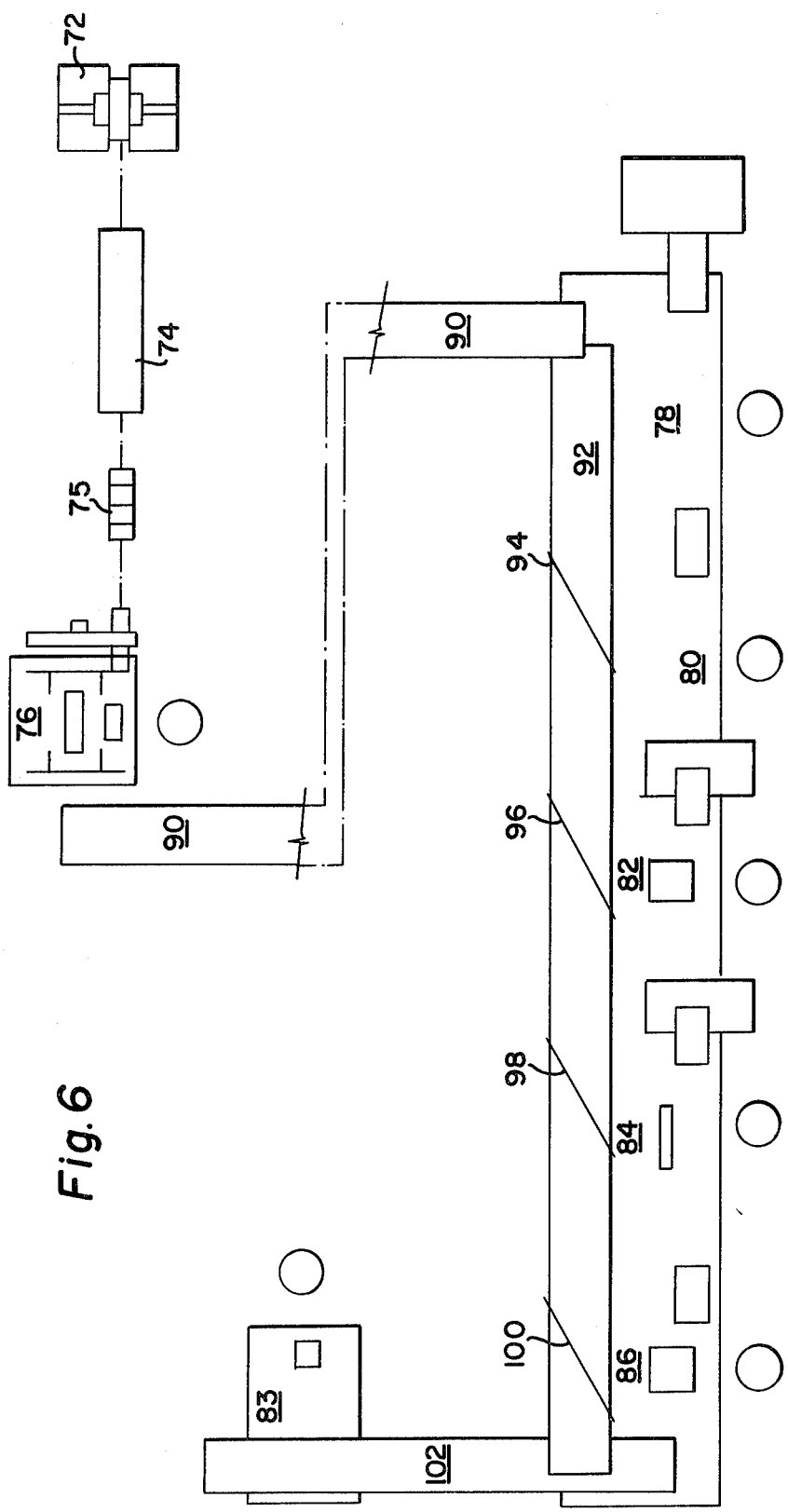
FIG. 6 is a schematic illustration of a manufacturing process for producing the structure of FIG. 1.
Figure 7:
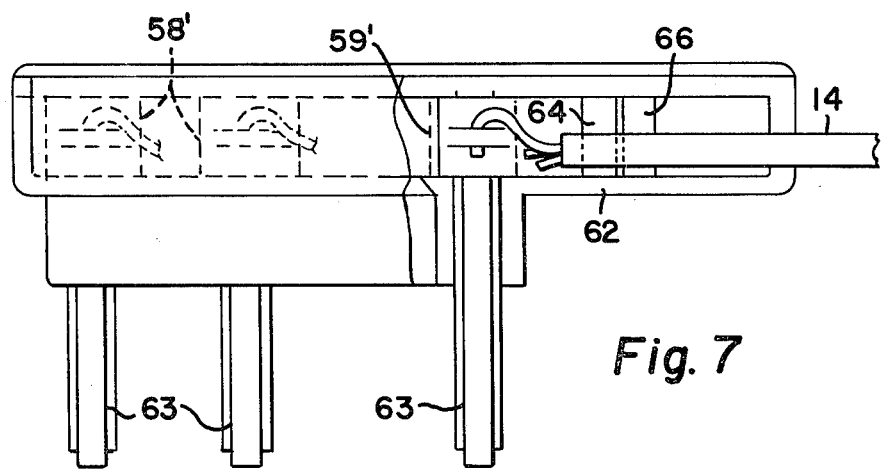
FIG. 7 is an enlarged cross sectional view of the electrosurgical generator plug of the invention.
Figure 8:
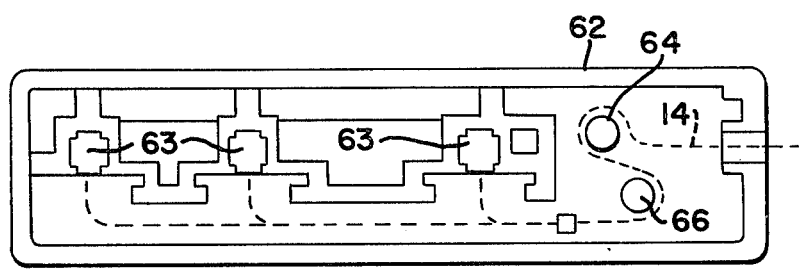
FIG. 8 is a top plan view of the plug shown in FIG. 6 with the distal end cap removed.
Figure 9:
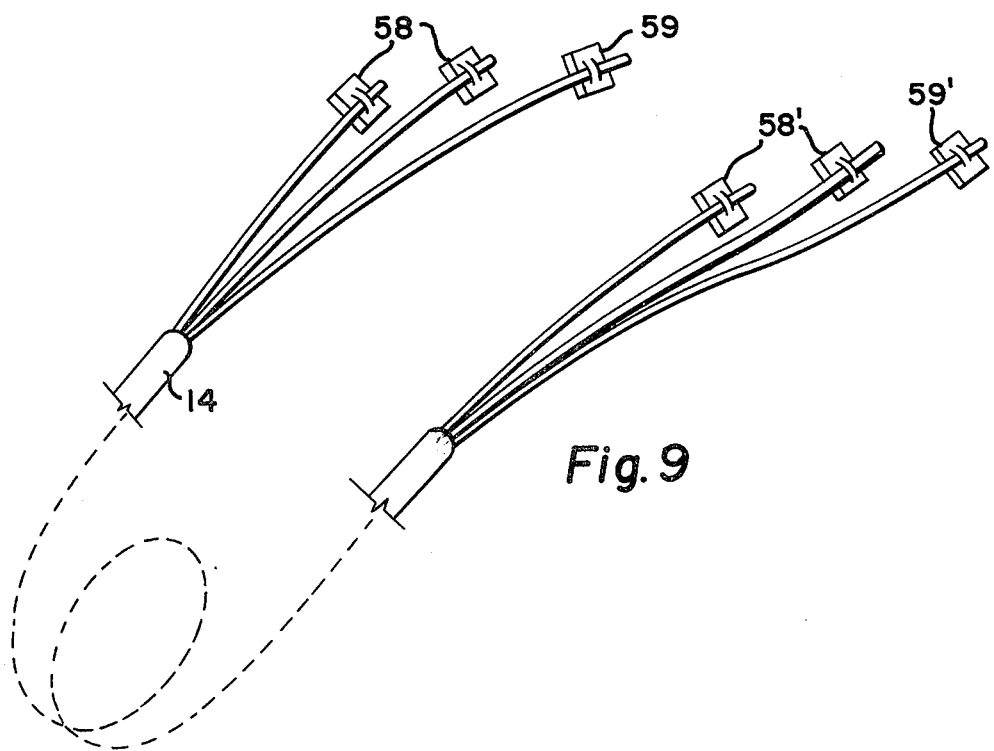
FIG. 9 is a perspective view of the cable, wires, and contact clips.

The process of manufacturing the present inventive apparatus is illustrated by way of an assembly line diagram shown in FIG. 6. Initially, an insulated, shielded three-conductor cable is dispensed from stock reel 72 and drawn through ultrasonic cleaner 74 to a stock leveler 75. At press 76, three wire clips, as previously described, are placed on the opposite ends of the cable 14. The clip can be maintained in a hopper from stock or carried into the hopper from an automatic punching and forming assembly. A press, preferably a 25T-press, is operated by hand, although any other well-known manner of attaching contacts to the cable may be used. After the six contact clips are attached to the cable, the cable is placed on conveyor 90 and carried to electrical mounting position 78.

At position 78, the spring contact 56 is mounted on supports 44 and 46 and common conductor clip 59 is mounted to support 46 of right half 22, at which time the assembly is then placed on conveyor 92.

At position 80, gate 94 across conveyor 92 forces the partly assembled unit to leave conveyor 92. At this point, the two fixed clips 58 are mounted to contact mounts 38 within right half 22 and the wires and cable correctly positioned in chamber 67. The assembly is then placed on conveyor 92 beyond gate 94.

Another diagonal gate 96 is reached at station 82. At this point, the left half 24 is positioned on top of the right half 22 to form the housing and the halves are welded by sonic or other well-known methods to create a unitary housing 20. The assembly is then again returned to conveyor 92.

When another gate 98 is encountered, the assembly leaves conveyor 92 at station 84, where generator connector 18 is attached to the free end of cable 14. Specifically, the body of connector 18 is provided three wire contacts already coupled to the conductor contacts on cable 14, and three generator contact pins. The assembly is again placed on conveyor 92.

The assembly encounters the last gate 100 at work station 86. Here the seal 54, switch body 51, and switch cap 64 are installed at the switch seat 60 defined by the housing 20. The switch cap 64 is welded by sonic or other well-known methods to the housing 20 in order to establish a positive joint and maintain the seal 54 in place to prevent accumulation of liquids within housing 20, as well as eliminate electrical contact between spring contact 56 and the hand of the treating physician.

Following this step, the completed inventive apparatus 10 is placed on conveyor 102 and carried to work station 88 which is a quality control station. At this point, each completed assembly is tested for appropriate mechanical and electrical characteristics, and properly functioning devices are then sent on for sterilization, packaging, and distribution. The physician may insert a monopolar blade with suitable characteristics for the particular surgical procedure at hand.

It should be noted that the steps of the procedure can be interchangeable without departing from the scope of the invention. Furthermore, these steps can be interchanged and are equivalent. In the foregoing description, the invention has been described with reference to a particular preferred embodiment, although it is to be understood that the specific details shown are merely illustrative and the invention may be carried out in other ways without departing from the true spirit and scope of the following claims.

What is claimed is:

1. A process for manufacture of an electrosurgical pencil, comprising the steps of:
    (a) attaching wire contact clips to wire ends of a multi-conductor cable;
    (b) placing a spring contact member within a housing portion of a two piece electrosurgical pencil casing;
    (c) mounting said wire contact clips to said housing portion adjacent to and spaced from said spring contact member;

(d) placing a second housing portion on said first housing portion, and sealing the second housing portion to said first housing portion to complete a casing;

(e) selecting an asymmetric generator plug, and coupling the contact clips on the opposite ends of said wires to said plug;

(f) mounting a seal, switch body, and cap frame to a switch seat defined in said casing adjacent said spring contact; and (g) securing said cap frame to said casing, retaining said seal and switch body.

2. A process for manufacturing an electrosurgical scalpel pencil comprising the steps of:

(a) withdrawing and severing from a stock reel a cable portion comprising at least a common conductor, a first signal conductor, and a second signal conductor;

(b) connecting wire clips to each end of said common conductor, first signal conductor, and second signal conductor;

(c) placing a spring contact and a clip attached to said common conductor at one end of said cable to a plastic electrosurgical pencil body portion, so that said clip restrains said spring contact and maintains electrical contact therebetween;

(d) placing clips attached to said first signal conductor and said second signal conductor at said one end of said cable within said body portion of said plastic electrosurgical pencil body, spaced apart from one another and adjacent said spring contact;

(e) securing a second body portion of said plastic electrosurgical pencil to said first body portion of said plastic electrosurgical pencil to create a unitary body;

(f) placing wire clips attached to said common conductor, first signal conductor, and second signal conductor at the opposite end of said cable in a generator connector adapted for electrical connection to an electrosurgical generator; and (g) attaching a seal and rocker switch to a switch seat defined in said pencil body above said spring contact, so that finger pressure on said rocker switch will deflect said spring contact to make electrical connection with either of said wire clips attached to said first signal conductor or said second signal conductor within said pencil body.

3. The process of claim 2, wherein said rocker switch comprises a fulcrum pin, switch body atop said fulcrum pin, and a switch frame surrounding said switch body retaining said switch body, fulcrum pin, and seal to said pencil body.

4. The process of claim 3, wherein said switch frame is sealed sonically to said pencil body.

5. The process of claim 2, wherein said second body portion of said electrosurgical pencil is secured to said first body portion by sonically welding the plastic portions together.

6. The process of claim 2, wherein the spring contact and clip of step (c) engage each other.

7. The process of claim 2, wherein the wire clips are formed with a stamped out portion adapted to hold a conductor end.

8. The process of claim 2, wherein said seal is a rubber gasket.

9. The process of claim 2, wherein said seal and rocker switch are attached by securing a switch frame to said pencil body.

10. The process of claim 2, including the step of sterilizing said electrosurgical scalpel pencil after it is constructed.

11. The process of claim 10, wherein said sterilization is accomplished by gamma radiation.

* * * * *